United States Patent [19]

Curry et al.

[11] 4,001,392
[45] Jan. 4, 1977

[54] HAIRDRESSINGS

[75] Inventors: Kenneth Vasey Curry, Camberley; Ahamado Ismail Sahir, Isleworth, both of England

[73] Assignee: Lever Brothers Company, New York, N.Y.

[22] Filed: Jan. 21, 1970

[21] Appl. No.: 4,761

[30] Foreign Application Priority Data

Jan. 31, 1969 United Kingdom ............... 5431/69

[52] U.S. Cl. .................. 424/47; 424/70; 424/71
[51] Int. Cl.$^2$ ......................... A61K 7/11
[58] Field of Search ............... 424/47, 70, 78, 71, 424/DIG. 1, DIG. 2; 167/87

[56] References Cited

UNITED STATES PATENTS

| | | | |
|---|---|---|---|
| 2,425,845 | 8/1947 | Toussaint et al. | 260/615 |
| 2,771,394 | 11/1956 | Mehaffey | 424/74 |
| 2,983,650 | 5/1961 | Rubin | 424/47 X |
| 2,996,471 | 8/1961 | Reiter et al. | 424/78 X |
| 3,145,147 | 8/1964 | Glickman | 424/47 |
| 3,188,275 | 6/1965 | Erlemann | 424/71 |
| 3,330,730 | 7/1967 | Hernandez | 424/70 X |
| 3,346,457 | 10/1967 | Dasher et al. | 424/47 |
| 3,427,382 | 2/1969 | Haefele | 424/71 |

FOREIGN PATENTS OR APPLICATIONS

| | | | |
|---|---|---|---|
| 1,061,034 | 3/1967 | United Kingdom | 424/71 |
| 1,117,129 | 6/1968 | United Kingdom | 424/71 |

OTHER PUBLICATIONS

"UCON" Fluids and Lubricants, Carbide and Carbon Chemicals Corp., New York, Received 1950, pp. 3–6 and 17.

*Primary Examiner*—Dale R. Ore
*Attorney, Agent, or Firm*—Arnold Grant

[57] ABSTRACT

A hairdressing composition capable of holding the hair in place and imparting a luster to the hair. The composition comprises an alcoholic or aqueous alcoholic solvent in which there is completely dissolved at least 0.1% by weight of the composition of a film-forming resin as hair fixative agent and at least 2% by weight of the composition of a water-insoluble hair luster aid which is incompatible with the resin. The alcohol is preferably ethyl alcohol or isopropyl alcohol and the film-forming resin is preferably water-soluble.

8 Claims, No Drawings

HAIRDRESSINGS

This invention relates to hairdressings.

The inclusion of hair fixative agents, such as synthetic resins, in hairdressings is well-known, such hairdressing compositions usually taking the form of a solution of the resin in a volatile solvent. These solutions can be applied to the hair either before or after styling and on evaporation of the solvent a film of the resin remains behind on the hair and this serves to keep the hair in place. It has also been proposed to include in such resin-containing hair fixative products an agent intended to impart lustre or gloss to the hair, referred to hereafter as a lustre aid.

It is an object of the invention to provide an improved hairdressing of the type containing a resin and a lustre aid, and in particular to provide a product of this kind giving superior gloss effects whilst still exhibiting good hair setting properties.

Accordingly the present invention provides a hairdressing composition comprising an alcoholic or aqueous alcoholic solvent in which there is completely dissolved at least 0.1% by weight of the composition of a film-forming resin and at least 2% by weight of the composition of a water-insoluble lustre aid which is incompatible with the resin.

By the lustre aid being incompatible with the resin we mean that the lustre aid is immiscible with the resin so that it does not plasticise or soften the resin or otherwise substantially modify the hair-fixative properties of films of the resin.

Film-forming agents which can be used in the hairdressing preparations of the invention include water-soluble and water-insoluble synthetic resins. Examples of water-insoluble resins that can be used are certain copolymers of vinyl pyrrolidone and vinyl acetate, copolymers of vinyl alkyl ethers and maleic anhydride, and copolymers of vinyl actate and crotonic acid. As examples of the water-soluble resins, which are preferred, are mentioned polyvinyl pyrrolidone, various grades of vinyl pyrrolidone/vinyl acetate copolymer, and certain insoluble resins neutralised to render them soluble, particularly the water-soluble neutralised copolymers of vinyl acetate and crotonic acid and the water-soluble neutralised copolymers of vinyl alkyl (e.g. methyl) ethers and maleic anhydride.

To render the copolymer of vinyl acetate and crotonic acid water-soluble it is preferably neutralised with an aminohydroxy compound, for example 2-amino-2-methyl-1,3-propanediol or 2-amino-2-methyl-1-propanol in accordance with British patent specification No. 856,403. The recommended amount of neutralising agent to give good water-soluble characteristics to the neutralised resin is 10 to 16% by weight of the copolymer. These neutralising agents may also be used to render soluble other water-insoluble resins.

Preferred lustre aids for inclusion in hairdressings in accordance with the invention for imparting gloss or shine to the hair are polyethylene-polypropylene glycol ethers. These materials are polyalkylene glycols containing ethylene glycol units and propylene glycol units and are availble commercially from Union Carbide Corporation being called Ucon Fluids: it is the members of the LB series of Ucon Fluids, i.e. the water-insoluble ones, that are to be used in hairdressing products of the present invention. These glycol ethers are available in a range of viscosities. Preferred materials are those having viscosities of from 10 to 400 centistokes at 38° C (100° F). Particularly preferred is the material Ucon Fluid LB 625 which has a viscosity of 135 centistokes at 100° F. The water-insoluble polyethylene-polypropylene glycol ethers have been found to be incompatible with a wide variety of resin fim-forming agents, including all those mentioned above. Other lustre aids can, however, be employed with the appropriate resins and as an example is mentioned the combination of diisopropyl adipate and copolymers of vinyl acetate and crotonic acid.

The preferred alcohols employed in the hair dressing preparations of the invention are the lower $C_1$–$C_4$ aliphatic alcohols, for example ethyl alcohol (such as in the form of industrial methylated spirit) and isopropyl alcohol.

An essential feature of hairdressing preparations of this invention is that the lustre aid is incompatible with the resin. The consequence of this incompatibility is that not only does the lustre aid not cause plasticization of the resin with consequent loss of setting properties of the resin, but that because the lustre aid forms, on evaporation of the solvent a separate phase, it can impart a glossy appearance to the hair if it is present in the composition in a sufficient amount. We have found that the lustre aid should be present to the extent of at least 2% by weight of the composition if the composition is to give the superior gloss effects which it is an object of this invention to provide.

In spite of the relatively high level of lustre aid present in the hairdressing compositions of this invention, and particularly in the specific products details of which are given later in the Examples, it is also a feature of this invention that the lustre aid is in the completely dissolved state in the solvent. Thus the resin, lustre aid and solvent form a homogeneous mixture which is of importance in ensuring uniform application of both resin and lustre aid and in obtaining the desired separation of the product into two phases on drying, as well as in enabling a product of greater visual appeal and consumer acceptability to be produced which is of importance particularly when the hairdressing composition of the invention is contained in transparent containers.

The hairdressing of the invention may take various forms. For example, it may be in the form of a lotion or gel, aerosol quick-break foam product, or in the form of an aerosol spray.

Hairdressing products of the invention in the lotion form desirably comprise: alcohol 30 to 70%, preferably 40 to 60%; water 20 to 40%, preferably 20 to 30%; film-forming agent 0.1 to 5%, preferably 0.5 to 3%; and the lustre aid 5 to 30%, preferably 10 to 25%.

When in the form of a quick-break aerosol foam product, suitable amounts of the above ingredients are: alcohol 10 to 70%, preferably 40 to 60%; water 1 to 30%, preferably 15 to 25%; film-forming agent 0.1 to 5%, preferably 0.5 to 3%; and the lustre aid 2 to 15%, preferably 2 to 6%. This product will, of course, also contain an appropriate amount of a surface-active agent to provide foaming on discharge of the aerosol, and, of course, liquefied gaseous propellant such as the conventionally used fluorinated hydrocarbons.

For a product in the form of an aerosol spray the ranges of the ingredients are desirably; alcohol 30 o 70%, preferably 45 to 60%; water 0 to 25%, preferably 10 to 18%; film-forming agent 0.1 to 5%, preferably 0.5 to 2%, and lustre aid 2 to 20%, preferably 2 to 8%. Any appropriate amount of liquefied gaseous propellant will also be included in this product.

The well-known carboxyvinyl polymeric thickening agents known under the trade name Carbopol can be used to form hairdressing products of the invention in the form of alcoholic gels. Suitable ranges for amounts of the ingredients of such gel forms are: alcohol 10 to 70%, preferably 30 to 60%; water 10 to 70%, preferably 30 to 60%; film-forming agent 0.1 to 5% preferably 0.5 to 2%; lustre aid 2 to 15%, preferably 2 to 10; carboxyvinyl polymer thickening agent 0.1 to 4%, preferably 0.2 to 2%; and neutralising agent for the carboxyvinyl polymer 0.1 to 5%, preferably 0.2 to 2.5%.

In the hairdressing preparations of this invention it is required that both the resin an lustre aid are completely dissolved in the alcoholic or aqueous alcoholic solvent. Should the lustre aid and/or resin have only a limited solubility in aqueous alcoholic solvents, it is necessary in such cases to choose the appropriate levels of lustre aid, resin, alcohol and water within the limits indicated above, so that both resin and lustre aid are in the completely dissolved state.

When applying products which contain less than about 15% water, it is desirable in order to obtain good spreading of the product over the hair to wet the hair and this may be done either before applying the hairdressing or afterwards, such as by passing a wetted comb through the hair.

Hairdressing compositions in accordance with the invention may include minor amounts of various other ingredients, for example germicides, perfumes, colouring agents, and resin plasticisers.

The following examples of hairdressing products illustrate the invention. All percentages are by weight.

EXAMPLE 1

The following is an example of a hairdressing product of the invention in the form of an aqueous alcoholic lotion.

| Ingredient | % |
|---|---|
| Water-insoluble polyethylene-polypropylene glycol ether (Ucon Fluid LB 625) | 20.0 |
| Copolymer of vinylacetate and crotonic acid (National Starch Resyn 28 –1310) | 2.7 |
| 2-amino-2-methyl-1,3-propanediol | 0.3 |
| Industrial Methylated Spirit (perfumery grade) | 49.0 |
| Colour | q.s. |
| Perfume | q.s. |
| Water | to 100.0 |

The lotion was manufactured in the following manner. The resin was first added to a solution of the neutralising agent in part of the alcohol. The glycol ether was dissolved in the remaining alcohol and to this the resin solution was added and stirred in. Water, colour and finally perfume were then added and the mixture stirred to give a homogeneous clear product.

EXAMPLE 2

The following is an example of the hairdressing composition of the invention in the form of a quick-breaking aerosol foam.

| Ingredient | % |
|---|---|
| Water-insoluble polyethylene-polypropylene glycol ether (Ucon Fluid LB 625) | 3.0 |
| Copolymer of vinylacetate and crotonic acid (National Starch Resyn 28 –1310) | 0.9 |
| 2-amino-2-methyl-1,3-propanediol | 0.1 |
| Industrial Methylated Spirit (perfumery grade) | 59.0 |
| Water | 23.5 |
| Mixture of cetyl and stearyl alcohols and their ethylene oxide condensates (Polawax A 31) | 3.5 |
| Propellant | 10.0 |

A suitable propellant is a mixture of 40% dichlorodifluoromethane and 60% dichlorotetrafluoroethane.

EXAMPLE 3

The following is an example of a hairdressing composition of the invention in the form of an aerosol spray.

| Ingredient | % |
|---|---|
| Water-insoluble polyethylene-polypropylene glycol ether (Ucon Fluid LB 625) | 4.50 |
| Copolymer of vinylacetate and crotonic acid (National Starch Resyn 28 –1310) | 0.99 |
| 2-amino-2-methyl-1,3-propanediol | 0.11 |
| Industrial Methylated Spirit (perfumery grade) | 56.20 |
| Water | 15.70 |
| Propellant | 22.50 |

The propellant is suitably that given in Example 2.

EXAMPLE 4

The following is an example of a hairdressing composition of the invention in the form of an essentially anhydrous aerosol spray.

| Ingredient | % |
|---|---|
| Water-insoluble polyethylene-polypropylene glycol ether (Ucon Fluid LB 625) | 6.00 |
| Copolymer of vinylacetate and crotonic acid (National Starch Resyn 28 –1310) | 0.36 |
| 2-amino-2-methyl-1,3-propanediol | 0.04 |
| Industrial Methylated Spirit (perfumery grade) | 38.60 |
| Propellant | 55.00 |

A suitable propellant is a mixture of 65% trichlorofluoromethane and 35% dichlorodifluoromethane.

This composition is preferably applied to pre-wetted hair.

EXAMPLE 5

The following is an example of a hairdressing composition of the invention in the form of a clear non-pourable gel.

| Ingredient | % |
|---|---|
| Diisopropyl adipate | 5.0 |
| Copolymer of vinylacetate and crotonic acid (National Starch Resyn 28 –1310) | 0.9 |
| 2-amino-2-methyl-1,3-propanediol | 0.1 |
| Industrial Methylated Spirit (perfumery grade) | 48.8 |
| Carboxyvinyl polymer (Carbopol 940) | 1.6 |
| Triethanolamine | 1.4 |
| Water | 42.2 |

The products of the above Examples all had good hair-fixative properties and imparted a glossy, healthy appearance to hair. In all these products the resin and lustre aid were completely dissolved in the solvent.

After application of the hairdressings of the Examples to the hair (in the case of the produce Example 4, the hair being wetted either before or after application of the product), the hair dries by evaporation of the alcohol and then of the water and the resin and the lustre aid separate into two distinct phases. It is believed that it is because this separation occurs the products in accordance with the invention exhibit particularly good grooming properties.

In the work leading up to this invention a large number of hairdressings containing different combinations of hair setting resin and lustre aid were tested and those containing water-insoluble resin-incompatible lustre aids were superior in that the lustre aid did not substantially adversely affect the hair setting properties of the resin or the setting aid substantially reduce the gloss-imparting properties of the lusre aid. The inferior combinations all exhibited a loss of hair-fixative properties arising from the lustre aid having a plasticising or softening action on the hair setting resin. Typical of combinations where this softening effect on the resin was encountered were combinations of water-soluble polyethylene-polypropylene glycol ethers with either water-soluble neutralised copolymers of vinyl acetate and crotonic acid or copolymers of vinyl pyrrolidone and vinyl acetate. This plasticising action of the lustre aid also resulted in a loss of hair lustre.

A further example of a hair preparation which has been investigated but found to be inferior to preparations of the present invention was one in accordance with U.S. Pat. No. 3,346,457 and consisting essentially of an ethanolic solution of polyvinyl pyrrolidone and squalene. Squalene has a limited solubility in ethanol and ethanol/water mixtures and it is not possible to dissolve completely in these solvent even 0.5% by weight of squalene. Such preparations are not able to give the superior lustre effects produced by the compositions of this invention.

What we claim is:

1. A hairdressing composition for holding and imparting lustre to the hair comprising from 10 to 70% of a lower aliphatic alcohol having from 1 to 4 carbon atoms; up to 40% water; from 0.1 to 5% of a film-forming agent selected from the group consisting of a copolymer of vinyl pyrrolidone and vinyl acetate, a copolymer of vinyl acetate and crotonic acid, polyvinyl pyrrolidone and a water soluble neutralized copolymer of a vinyl alkyl ether and maleic anhydride; and, from about 2 to about 30% of a lustre aid being selected from the group consisting of polyethylene-polypropylene glycol ether having a viscosity of from 10 to 400 centistokes at 100° F and diisopropyl adipate.

2. A hairdressing composition as claimed in claim 11 in the form of an alcoholic lotion comprising 30 to 70% by weight of a lower aliphatic alcohol having from 1 to 4 carbon atoms, 20 to 40% by weight of water, 0.1 to 5% by weight of the film-forming resin and 5 to 30% by weight of the lustre aid.

3. A hairdressing composition as claimed in claim 11 in the form of an aerosol quick-break foam product, comprising 10 to 70% by weight of a lower aliphatic alcohol having from 1 to 4 carbon atoms, 1 to 30% by weight of water, 0.1 to 5% by weight of the film-forming resin, 2 to 15% by weight of the lustre aid, and effective amounts of a surface-active agent and liquified gaseous propellant to permit the composition to be discharged from an aerosol container in the form of a quick-breaking foam.

4. A hairdressing composition as claimed in claim 1 in the form of an aerosol spray product, comprising 30 to 70% by weight of a lower aliphatic alcohol having from 1 to 4 carbon atoms, 0 to 25% by weight of water, 0.1 to 5% by weight of the film-forming resin and 2 to 20% by weight of the lustre aid together with an appropriate amount of a gaseous liquefied propellant.

5. A hairdressing composition as claimed in claim 1, wherein the alcohol is selected from the group consisting of ethyl alcohol and isopropyl alcohol.

6. A hairdressing composition as claimed in claim 1, wherein the film-forming resin is water-soluble.

7. A hairdressing composition as claimed in claim 6 wherein the film-forming resin is selected from the group consisting of polyvinyl pyrrolidone, a copolymer of vinyl pyrrolidone and vinyl acetate, a copolymer of vinyl acetate and crotonic acid, and a neutralised copolymer of a vinyl alkyl ether and maleic anhydride.

8. A hairdressing composition as claimed in claim 1, wherein the hair lustre aid is a polyethylene-polypropylene glycol ether.

* * * * *